United States Patent [19]

Victor

[11] Patent Number: 4,636,199
[45] Date of Patent: Jan. 13, 1987

[54] DEVICE FOR INSERTING A CATHETER WITHIN THE INTERCOSTAL SPACE

[76] Inventor: Lyle D. Victor, 18181 Oakwood Blvd., Dearborn, Mich. 48124

[21] Appl. No.: 628,792

[22] Filed: Jul. 9, 1984

[51] Int. Cl.⁴ ............................................. A61M 5/00
[52] U.S. Cl. .................................... 604/164; 604/170
[58] Field of Search .............................. 604/164–166, 604/170, 171, 158, 264; 128/772, 657

[56] References Cited

U.S. PATENT DOCUMENTS

| | | | |
|---|---|---|---|
| 3,539,034 | 11/1970 | Tafeen | 604/164 |
| 3,633,579 | 1/1972 | Alley et al. | 604/164 X |
| 3,903,885 | 9/1975 | Fuchs | 604/165 X |
| 3,960,153 | 6/1976 | Carey et al. | 604/164 |
| 3,993,079 | 11/1976 | Henriques de Gatztanondo | 604/164 |
| 4,077,412 | 3/1978 | Moosun | 604/164 X |
| 4,230,123 | 10/1980 | Hawkins, Jr. | 604/165 X |
| 4,239,042 | 12/1980 | Asai | 604/164 |
| 4,417,886 | 11/1983 | Frankhouser et al. | 604/164 X |

Primary Examiner—Stephen C. Pellegrino
Attorney, Agent, or Firm—Gifford, Groh, VanOphem, Sheridan, Sprinkle & Dolgorukov

[57] ABSTRACT

The present invention provides a device for inserting a catheter within the intercostal space to withdraw a fluid from that space. A hollow needle of a syringe is first inserted into the intercostal space to determine the presence or absence of the fluid and, if present, a guide wire is inserted through the needle, into the space and then the needle is withdrawn. A tubular catheter is then positioned over an elongated trocar so that the trocar carries the catheter. In addition, the trocar includes an axial throughbore designed to receive the guide wire. Consequently, with the guide wire positioned through the trocar throughbore, one end of the trocar as well as the catheter are forced into the intercostal space after which the trocar is withdrawn from the catheter. The catheter is then connected to suction equipment or the like to drain the intercostal space in the desired fashion.

2 Claims, 3 Drawing Figures

DEVICE FOR INSERTING A CATHETER WITHIN THE INTERCOSTAL SPACE

BACKGROUND OF THE INVENTION

I. Field of the Invention

The present invention relates generally to devices for inserting catheters and, more particularly, to a device for inserting a catheter into the intercostal space.

II. Description of the Prior Art

There are many situations where it is necessary to drain the intercostal space, i.e. the space between the lung and the chest wall, of unwanted fluids. Such fluids can consist of air, pus, blood and the like. Furthermore, the failure to rapidly drain the intercostal space of unwanted fluids can result in further injury or even death of the patient.

In order to drain the intercostal space of unwanted fluids, typically a catheter is inserted into the intercostal space and is connected with appropriate suction or drainage equipment. Such catheters are typically inserted through the chest through the rib cage and thus requires not only tissue cutting but also involves some risk to the patient. For example, the improper insertion of the catheter can result in a punctured lung or other injuries to the patient.

For these reasons, a medical surgeon is ususally required to insert the catheter into the intercostal space, particularly since many general practitioners and many medical specialists other than surgeons are reluctant to engage in such surgical procedures. However, in many instances a surgeon is unavailable to insert the catheter and yet the catheter must be immediately inserted in order to prevent rapid, life threatening air and fluid accumulation.

SUMMARY OF THE PRESENT INVENTION

The present invention provides a device for inserting a catheter within the intercostal space which can be easily and safely used by general practitioners and medical specialists other than surgeons.

In brief, in the present invention a hollow needle of a syringe is first inserted into the intercostal space to determine the presence and type of fluid. If no fluid or air is found, the needle is simply withdrawn and the procedure to insert the catheter terminated or, alternatively, a needle puncture into another region of the intercostal space is attempted.

Conversely, if fluid is found within the intercostal space, the doctor inserts a guide wire through the needle so that one end of the guide wire is positioned within the intercostal space while the other end extends exteriorly of the patient. The needle is then withdrawn over the guide wire.

In order to insert the catheter into the intercostal space, the present invention provides an elongated trocar which is dimensioned to be positioned within the catheter so that a pointed end of the trocar protrudes outwardly from one end of the catheter and so that the trocar carries the catheter. In addition, the trocar includes an axial throughbore dimensioned to slidably receive the guide wire.

In order to insert the catheter into the intercostal space, a small incision is made in the skin at the exit point of the guide wire and the guide wire is then threaded through the trocar bore. The trocar, together with the catheter, is then forced into the patient while being guided by the guide wire until the end of the catheter is positioned within the intercostal space. Thereafter, the trocar is removed from the catheter and the catheter is attached to conventional suction or drainage equipment in order to drain the unwanted fluid.

In the preferred form of the invention, the end of the trocar opposite from its pointed end is preferably flared outwardly and its outwardly flared portion cooperates with a similarly outwardly flared portion on the catheter. The flared portion of the trocar thus prevents the catheter from sliding along the trocar during its insertion into the intercostal space. Furthermore, the outwardly flared portion on the trocar provides a relatively wide surface which allows the doctor to firmly engage the trocar and to push the trocar through the patient's tissue and into the intercostal space in the desired fashion.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE INVENTION

Figure 1:
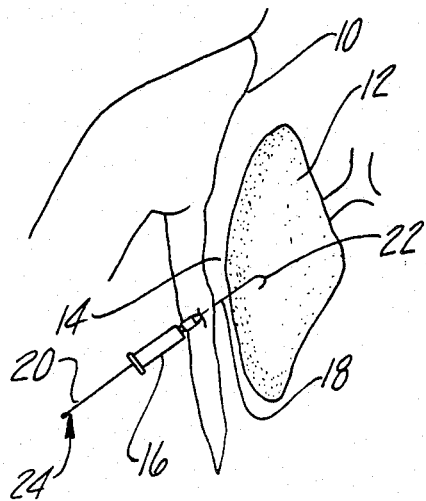
FIG. 1 is a fragmentary view illustrating steps for inserting the catheter.

With reference first to FIG. 1, a portion of a human patient 10 is thereshown having a lung 12 contained within the intercostal space 14 of a human body. The accumulation of unwanted fluids, such as air, blood or pus, within the intercostal space 14 must be removed in order to prevent serious injury or even death to the patient.

In order to remove unwanted fluids from the intercostal space 14, a syringe 16 having a hollow needle 18 is first inserted into the intercostal space 14. The plunger of the syringe 16 is then retracted to take a sample to determine the existance and type of dluid within the intercostal space 14. If no fluid is found, the syringe 16 is simply removed and the medical process terminated or another region of the intercostal space entered.

Conversely, in the event that an unwanted fluid is found within the intercostal space 14, the syringe 16 is detached from the needle 18 and an elongated guide wire 20 is inserted through the needle 18 until one end 22 is positioned within the intercostal space 14 while its other end 24 extends exteriorly of the patient's body.

After insertion of one end of the guide wire 20 into the intercostal space 14, the needle 18 is withdrawn over the guide wire 20. Furthermore, the depth of insertion of the needle 18 necessary to withdraw fluid from the intercostal space 14 provides a measure of the required depth of insertion of the catheter 34 (FIGS. 2 and 3) necessary to reach the intercostal space 14.

Figure 2:
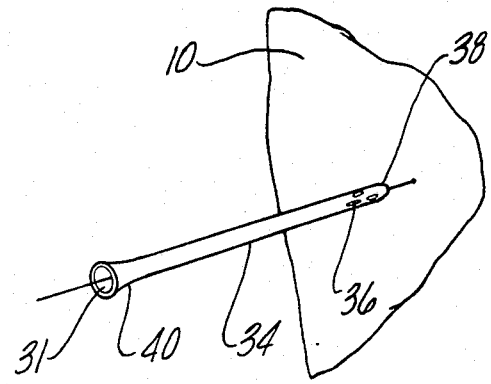
FIG. 2 is a fragmentary view illustrating a preferred embodiment of the invention.
Figure 3:
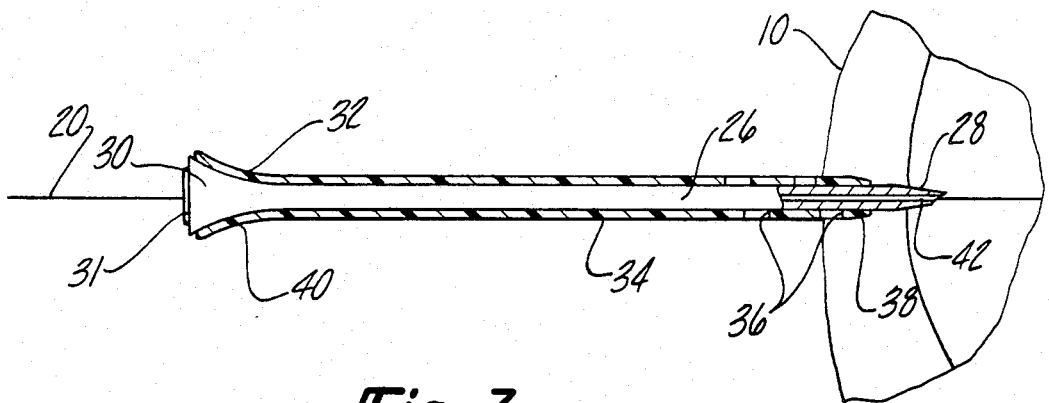
FIG. 3 is partial longitudinal sectional view of the preferred embodiment of the invention.

With reference now to FIGS. 2 and 3, in order to drain the fluid from the intercostal space 14, the present invention provides an elongated trocar 26 having a pointed end 28. The other end 30 of the trocar 26 preferably flares outwardly and terminates in a generally planar and circular flat surface 31 for a reason to be subsequently described.

Still referring to FIGS. 2 and 3, the trocar 26 is dimensioned to be positioned within an elongated catheter 34 having a plurality of drainage openings 26 at one end 38. In addition, the opposite end 40 of the catheter 34 is preferably outwardly flared at 32 and cooperates with the outwardly flared portion 30 of the trocar 26. Consequently, with the trocar 26 inserted through the catheter 34 to the position shown in FIG. 3, the abutment between the flared portions 32 and 30 prevents the further insertion of the trocar 26 through the catheter 34. Furthermore, the trocar 26 is dimensioned so that its pointed end 28 protrudes outwardly from the end 38 of the catheter 34.

With reference now to FIG. 3, the trocar 26 includes an elongated axial throughbore 42 which is dimensioned to slidably receive the guidewire 20. Consequently, in order to insert the catheter 34 into the intercostal space 14 a small incision is first made on the patient's skin at the exit point of the guide wire 20. The guide wire 20 is then threaded through the trocar throughbore 42 as shown in FIGS. 2 and 3 and the physician, using the flat surface 31 at the exterior end of the trocar 26 then pushes the trocar 26 together with its carried catheter 34 from the position shown in FIG. 2 and to the position shown in FIG. 3 and thus into the intercostal space 14. Furthermore, in doing so, the guide wire 20 guides the travel of the trocar 26 and prevents accidental puncture of the patient's lung 12 or other organs. In addition, the trocar 26 is inserted to a depth substantially equal to the distance between the patient's skin and the intercostal space 14 as determined during the insertion of the needle 18 as previously described.

With the end 38 of the catheter 34 positioned within the intercostal space 14 as described above, the trocar 26 is removed and the catheter 34 is slid several centimeters distally into the pleural space and the catheter 34 is then connected to suction equipment, if indicated, in order to drain the intercostal space 14 in the desired fashion.

From the foregoing, it can be seen that the present invention provides a device for inserting a catheter 34 within the intercostal space 14 which can be easily, simply and safely used by both non specialists and medical specialists other than surgeons. In particular, the guide wire 20 ensures that the trocar 26 with its carried catheter 34 is properly positioned within the intercostal space 14 and prevents puncture of the lung or other organs. Furthermore, the relatively wide flat surface 31 of the trocar forms a hand abutment surface which allows the secure and controlled insertion of the trocar 26 into the patient's body.

In addition, the cooperation between the outwardly flared portions 30 and 32 of the trocar 26 and catheter 34, respectively, ensures that the catheter 34 is inserted along with the trocar 26 into the intercostal space 14 and prevents any slippage of the catheter 34 with respect to the trocar 26 during insertion.

Having described my invention, however, many modifications thereto will become apparent to those skilled in the art to which it pertains without deviation from the spirit of the invention as defined by the scope of the appended claims.

I claim:

1. A surgical kit for draining fluid from the intercostal cavity of a human comprising:

a syringe having a plunger and a hollow needle, said needle being insertable into the intercostal space so that upon retraction of said syringe plunger, a sample of fluid within the intercostal space is withdrawn into the syringe, an elongated guide wire, one end of said guide wire being insertable through said hollow needle and into said intercostal space and said needle thereafter being removed, an elongated trocar having a pointed end and an outwardly flared portion at its other end, said trocar having a uniform crossectional shape between its pointed end and its outwardly flared portion, said trocar having an axial passageway from said pointed end and to said other end, said passageway being dimensioned to slidably receive the guide wire therethrough, an elongated hollow catheter, said catheter being open on one end and outwardly flared at its other end, said catheter having a throughbore of uniform shape between its open end and other end, said catheter being dimensioned to receive said trocar therethrough so that the pointed end of the trocar protrudes outwardly from said open end of the catheter, wherein said catheter throughbore is of a complementary size and shape to said trocar so that with said trocar positioned through said catheter, the catheter snugly fits over the trocar so that substantially the entire periphery of the catheter throughbore is in abutment with the trocar, and wherein said trocar includes a hand engagement surface at its other end adapted to be pushed and thereby simultaneously move said trocar and said catheter into the intercostal space, said hand engagement surface having an area substantially greater than a crossectional area of a midpoint of said trocar.

2. The invention as defined in claim 1 wherein said hand engagement surface is substantially planar and substantially perpendicular to an axis of said trocar.

* * * * *